United States Patent
Li et al.

(10) Patent No.: US 7,145,651 B2
(45) Date of Patent: Dec. 5, 2006

(54) APPARATUS FOR FLUORESCENCE SUBTRACTED RAMAN SPECTROSCOPY

(75) Inventors: Qun Li, Newark, DE (US); Sean Xiaolu Wang, Centerville, DE (US)

(73) Assignee: B & W Property Inc., Newark, DE (US)

( * ) Notice: Subject to any disclaimer, the term of this patent is extended or adjusted under 35 U.S.C. 154(b) by 0 days.

(21) Appl. No.: 11/227,432

(22) Filed: Sep. 16, 2005

(65) Prior Publication Data

US 2006/0061761 A1 Mar. 23, 2006

Related U.S. Application Data

(60) Provisional application No. 60/610,533, filed on Sep. 17, 2004.

(51) Int. Cl.
*G01J 3/44* (2006.01)
*G01N 21/65* (2006.01)
(52) U.S. Cl. ...................................... 356/301
(58) Field of Classification Search .............. 356/301
See application file for complete search history.

(56) References Cited

U.S. PATENT DOCUMENTS 3,914,055 A * 10/1975 Wolga et al. ............... 356/301
6,205,354 B1 3/2001 Gellerman et al.

* cited by examiner

*Primary Examiner*—F. L. Evans
(74) *Attorney, Agent, or Firm*—Blank Rome LLP

(57) ABSTRACT

A fluorescence subtracted Raman spectroscopy apparatus uses a wavelength modulated tunable filter as the spectrometer. The wavelength modulation results in an amplitude modulation on the detected optical signal. By using a frequency selective detection technique, the Raman signal is amplified and extracted from the fluorescence background.

12 Claims, 2 Drawing Sheets

APPARATUS FOR FLUORESCENCE SUBTRACTED RAMAN SPECTROSCOPY

REFERENCE TO RELATED APPLICATION

The present application claims the benefit of U.S. Provisional Application No. 60/610,533, filed Sep. 17, 2004, whose disclosure is hereby incorporated by reference in its entirety into the present disclosure.

FIELD OF INVENTION

The present invention generally relates to a Raman spectroscopy apparatus, and more specifically to a fluorescence subtracted Raman spectroscopy apparatus utilizing a wavelength modulated tunable filter as the spectrometer.

BACKGROUND OF THE INVENTION

Raman spectroscopy has been demonstrated to be a powerful non-invasive analytical technology for material characterization and identification. However, the strong fluorescence emission stimulated by the excitation laser often overwhelms the weak Raman signal, especially for composite materials. Several techniques have been proposed before to suppress the influence of the fluorescent emission. In one approach, the wavelength of the excitation laser is shifted to near-infrared (NIR) region as disclosed by Fujiwara M, et al. in *Applied Spectroscopy*, Vol. 40, p. 137, 1986. However, the Raman signal also becomes weaker, since the Raman scattering cross-section is inversely proportional to the fourth power of excitation wavelength. Another approach uses deep UV laser for Raman excitation as disclosed by Bowman W D, et al. in *Journal of Raman Spectroscopy*, Vol. 9, p. 369, 1980. But the lasers at this wavelength are both bulky and expensive.

Other approaches employ some laser modulation techniques. For example, by taking advantage of the fact that fluorescence emission and Raman emission have different decay times, the two spectra can be separated in the time domain by stimulating the material with an ultra short pulse laser as disclosed by Howard J, et al in *Journal of Physics E: Scientific Instruments*, Vol. 19, p. 934, 1986. This approach requires the pulse width of the laser to be in the order of pico-seconds. Commonly a nonlinear Kerr gate is used to separate the fluorescence emission from the Raman signal. Another approach, which is named as 'shifted excitation Raman difference spectroscopy' (SERDS), is proposed by Shreve A P, et al. in *Applied Spectroscopy*, Vol. 46, p. 707, 1992. In this approach, two similar Raman spectra with a small shift in wavelength are measured using a tunable laser. The difference between the two spectra is used to reconstruct the Raman spectrum. This approach utilizes the fact that the fluorescence spectra are generally independent of the excitation wavelength and its bandwidth, while Raman peaks occur at a fixed wavenumber distance from the excitation band and mimic its wavelength distribution exactly. A simpler but less effective approach is proposed by S. E. J. Bell, et al. in *Analyst*, Vol. 8, p. 1729, 1998. It obtains the difference Raman spectrum by shifting the position of the spectrometer, thus avoiding the use of the tunable laser.

SUMMARY OF THE INVENTION

There is thus a need in the art for a technique for fluorescence subtracted Raman spectroscopy which is effective without requiring expensive equipment like a tunable laser. Accordingly, it is an object of the invention to supply such a technique.

To achieve the above and other objects, the present invention provides a new method for fluorescence subtracted Raman spectroscopy, where a wavelength modulated tunable filter in combination with a photo detector is utilized as the spectrometer. The emission/scattering spectrum of the target is obtained by continuously scanning the central wavelength of the tunable filter and measuring the intensity of the selected wavelength component using the photo detector. In one preferred embodiment, a binary wavelength modulation is applied to the tunable filter, where the wavelength of the tunable filter is switched between two closely spaced wavelength values, i.e. $\lambda_1$ and $\lambda_2$. Due to variation of the target spectrum in wavelength domain, this wavelength modulation results in an amplitude modulation on the detected optical signal from the photo detector. The magnitude of the amplitude modulation depends on slope of the target spectrum. The fluorescence emission has a broadband, relatively flat spectrum, while the Raman scattering has a narrowband spectrum which matches with the linewidth of the excitation laser. As a result, the narrowband Raman signal is amplified and extracted from the broadband fluorescence background by employing the wavelength modulation technique. The modulation frequency of the detected optical signal is equal to the wavelength modulation frequency of the tunable filter. Thus it can be detected using ultra-sensitive frequency-selective detection techniques, such as the lock-in amplification technique. The noise generated by the dark current of the photo detector is filtered out by the frequency selection device, thus greatly improving the signal to noise ratio (SNR) of the obtained difference Raman spectrum.

The present invention can be applied to resonant Raman spectroscopy, which is a powerful tool for complex composite and hybrid structure analysis. In resonant Raman spectroscopy, the wavelength of the excitation laser is selectively matched with the absorption band of the specific component of the composite material to be detected. Thus, the Raman signal can be enhanced by 1000–10000 times. The specific component can be in very small quantities such that common Raman spectroscopy techniques cannot detect it. Unfortunately, the Raman enhancement is often accompanied by strong fluorescent emission. The wavelength modulation fluorescence subtraction technique provides an excellent solution to this problem. The present invention is also applicable to fluorescence subtraction in Raman spectral imaging.

BRIEF DESCRIPTION OF DRAWINGS

A preferred embodiment of the present invention will be set forth in detail with reference to the drawings, in which.

DETAILED DESCRIPTION OF THE PREFERRED EMBODIMENT

In one preferred embodiment of the current invention, the fluorescence subtracted Raman spectroscopy apparatus is built on an acousto-optic tunable filter (AOTF). The AOTFs have been widely used before for spectrometer applications as described by Xiaolu Wang, in 'Acousto-optic tunable filter: a powerful new tool in NIR spectroscopy for industrial on-line applications', *Opto News & Letters*, Vol. 37, No. 37–38, 1992. However, their use in the context of the present invention is considered to be novel. The wavelength of an AOTF can be easily tuned by adjusting the frequency of the radio frequency (RF) electronic signal applied on the AOTF crystal, which determines the frequency of the acoustic wave.

Figure 1:
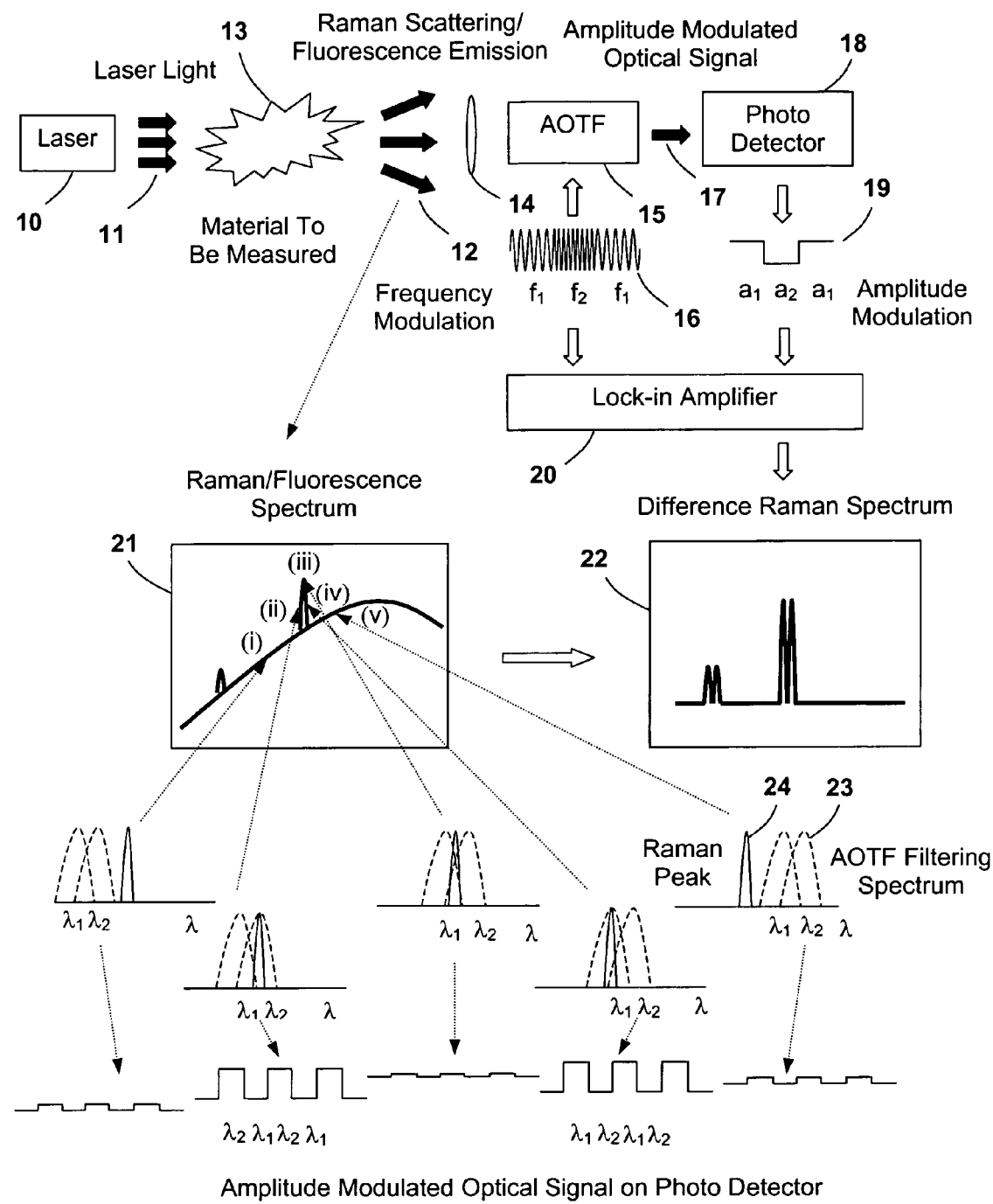
FIG. 1 illustrates one preferred embodiment of the current invention, where a wavelength modulated acousto-optic tunable filter (AOTF) is used to implement the fluorescence subtracted Raman spectroscopy apparatus.

A block diagram of the fluorescence subtracted Raman spectroscopy apparatus is illustrated in the upper portion of FIG. 1. A laser 10 produces a narrow linewidth laser light 11, which excites a Raman scattering and fluorescence emission 12 from the material to be measured 13. The Raman scattering and fluorescence emission 12 is collected by an optical system 14 and sent to an AOTF 15, which selects a wavelength component from the Raman/fluorescence spectrum 21. A frequency shift keying (FSK) modulation 16 is applied on the AOTF 15 to modulate its central wavelength in a binary mode. The FSK modulation 16 results in an amplitude modulated optical signal 17, which is detected by a photo detector 18. The detected signal 19 with amplitude modulation is further amplified by a lock-in amplifier 20 to acquire the difference Raman spectrum 22, which is constructed by recording the modulation amplitude of the optical signal at each AOTF central wavelength. The FSK modulation signal 16 is also sent to the lock-in amplifier 20 as a reference signal.

The operation of the fluorescence subtraction technique is further illustrated in the lower portion of FIG. 1. The frequency of the RF signal applied on the AOTF is modulated between two closely spaced values, i.e., $f_1$ and $f_2$, which results in a binary mode wavelength modulation between $\lambda_1$ and $\lambda_2$ on the AOTF filtering spectrum 23. The frequency spacing between $f_1$ and $f_2$ is fixed while the central frequency, i.e., $(f_1+f_2)/2$ is continuously tuned to scan the whole Raman/fluorescence spectrum. Under this FSK modulated RF signal, the detected optical signal on the photo detector is amplitude modulated at a frequency set by the FSK rate. The modulation amplitude is determined by the slope of the input spectrum. It is noted that although the Raman signal is weak in amplitude, it usually has a much narrower bandwidth than that of the fluorescent emission, as it resembles the spectrum of the excitation laser. Thus by employing this FSK modulation technique, the 'sharp' Raman signal is amplified while the 'flat' fluorescent signal is subtracted.

Some typical operation points of the wavelength modulated AOTF spectrometer and the corresponding modulation patterns of the detected optical signal are illustrated in FIG. 1, where the input spectrum adjacent to a Raman peak 24 is measured. When the central wavelength of the AOTF, i.e., $(\lambda_1+\lambda_2)/2$ is far away from the Raman peak (points (i) and (v)), the modulation amplitude is relatively small as it is mainly determined by the slope of the broadband fluorescence spectrum. When the AOTF filtering spectrum overlaps with the Raman peak, the modulation amplitude increases and reaches a maximum value at points (ii) and (iv). At point (iii) between points (ii) and (iv), the modulation amplitude decreases and reaches a minimum value as the AOTF filtering spectra at $\lambda_1$ and $\lambda_2$ are symmetrically positioned on the two sides of the Raman peak. The wavelength spacing between $\lambda_1$ and $\lambda_2$ can be optimized according to the bandwidth of the AOTF and the linewidth of the Raman signal as to achieve the maximum modulation amplitude. It should be noted that the average intensity of the detected optical signal is proportional to the spectral intensity of the fluorescence/Raman spectrum as indicated by the signal level variation for points (i)–(v).

In the current embodiment, the useful spectral information is encoded in an AC signal with fixed frequency set by the FSK modulation rate. A highly frequency-selective lock-in amplifier is used to extract and amplify the AC signal. Thus the white noise generated by the dark current of the photo detector is filtered out. This greatly increases the signal to noise ratio of the Raman spectrometer and makes it suitable for a variety of applications. One example of the application is carotenoid level detection in human skin. The human skin is a complicated composite comprising multiple chemical substances. As a result, the Raman scattering caused by carotenoid is often overwhelmed by a strong fluorescence background.

Figure 2:
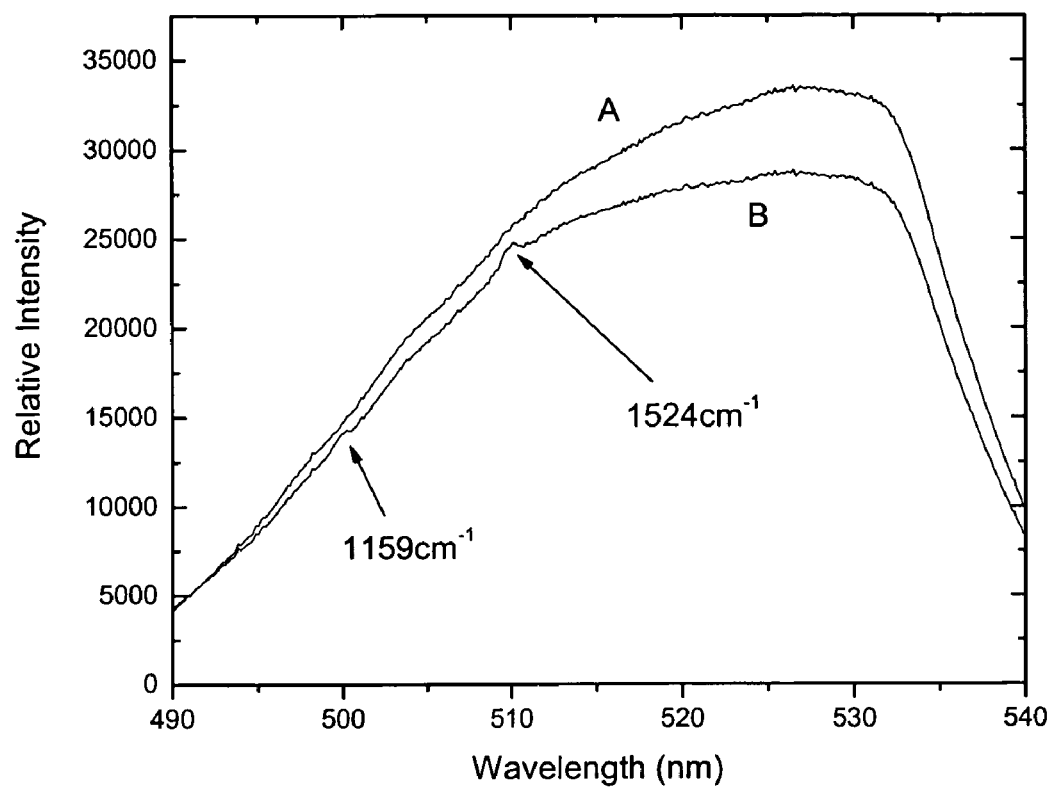
FIG. 2 shows the Raman/fluorescence spectrum of two human skin samples, where the Raman scattering of a carotenoid is hidden in a strong fluorescence background.

FIG. 2 shows the Raman/fluorescence emission spectra of two human skin samples excited by a 473 nm blue laser. For sample B, two characteristic carotenoid Raman peaks can be barely seen at 1159 $cm^{-1}$ and 1524 $cm^{-1}$. While for sample A, no Raman peak is observable under the fluorescence background. In prior arts as disclosed by Gellermann et al. in U.S. Pat. No. 6,205,354, "Method and Apparatus for Noninvasive Measurement of Carotenoid and Related Chemical Substance in Biological Tissue", a curve fitting method is used to subtract the fluorescence background, which may lead to errors as the fluorescence spectrum may vary in its shape for different human skins. The wavelength modulated AOTF spectrometer provides a solution to this problem since the measured difference Raman spectrum can be viewed as a derivative of the input Raman/fluorescence spectrum in its absolute value, where the weak Raman signal is amplified.

In other variations of the current embodiment, different frequency modulation techniques and frequency-selective amplification/detection techniques can be employed. The obtained difference Raman spectrum may appear in other forms. For example, the phase information of the modulated optical signal can be added into the modulation spectrum, making it a 'real' derivative of the input Raman/fluorescence spectrum. The original Raman emission spectrum of the material can also be reconstructed from the obtained difference Raman spectrum using certain curve fitting methods.

While various exemplary embodiments of the current invention have been set forth above, those skilled in the art who have reviewed the present disclosure will readily appreciate that other embodiments can be realized within the scope of the present invention. For example, the present invention is not confined to a specific instrument setup or sample type, such as the excitation laser, the operating wavelength, the type of the wavelength tunable optical filter, etc. Therefore, the present invention should be construed as limited only by the appended claims.

We claim:

1. A method for extracting a Raman signal from a fluorescence background in a Raman/fluorescence emission from a material, the method comprising:
   (a) exciting the Raman/fluorescence emission from the material by a laser light source;
   (b) measuring a Raman/fluorescence spectrum of the Raman/fluorescence emission using a spectrometer, wherein the spectrometer comprises a wavelength tunable optical filter for selecting a wavelength component of the Raman/fluorescence spectrum and a photo detector for measuring the Raman/fluorescence spectrum in the wavelength component selected by the wavelength tunable optical filter;

(c) modulating the wavelength component selected by the tunable filter in such a way that a modulated optical signal with a modulation amplitude representing a derivative of the Raman/fluorescence spectrum at a central wavelength of the tunable filter is detected by the photo detector;

(d) scanning the central wavelength of the tunable filter and recording the corresponding modulation amplitude for each wavelength to obtain a difference Raman spectrum; and (e) extracting and amplifying the Raman signal in accordance with the difference Raman spectrum.

2. The method of claim 1, wherein step (e) comprises reconstructing the original Raman spectrum from the difference Raman spectrum using curve fitting methods.

3. The method of claim 1, wherein step (c) comprises switching the wavelength of the tunable filter between two closely spaced values at a fixed frequency.

4. The method of claim 1, wherein the modulated optical signal is detected in step (c) using a frequency selective amplification/detection technique.

5. The method of claim 4, wherein the frequency selective amplification/detection technique comprises a lock-in amplification technique.

6. The method of claim 1, wherein step (d) comprises using phase information and amplitude information of the modulated optical signal for difference Raman spectrum construction.

7. The method of claim 1, wherein the wavelength tunable optical filter is an acousto-optic tunable filter (AOTF).

8. The method of claim 1, further comprising using the Raman signal for resonant Raman spectroscopy.

9. The method of claim 1, further comprising using the Raman signal for Raman spectral imaging.

10. A fluorescence subtracted Raman spectroscopy apparatus for extracting a Raman signal from a fluorescence background in a Raman/fluorescence emission from a material, the spectroscopy apparatus comprising:

(a) a laser for exciting the Raman/fluorescence emission from the material;

(b) a wavelength tunable optical filter for selecting a wavelength component from the Raman/fluorescence emission;

(c) a wavelength modulation device for modulating the wavelength component of the tunable filter and producing an amplitude modulated optical signal at an output of the tunable filter; and (d) a photo detector for detecting the amplitude modulated optical signal and for producing an output representing the fluorescence subtracted Raman signal.

11. The apparatus of claim 10, further comprising a frequency selective amplification/detection device for difference Raman spectrum extraction.

12. The apparatus of claim 11, wherein the frequency selective amplification/detection device comprises a lock-in amplifier.

* * * * *